US009044325B2

(12) United States Patent  
Palmer et al.

(10) Patent No.: US 9,044,325 B2  
(45) Date of Patent: Jun. 2, 2015

(54) ELBOW PROSTHESIS AND METHOD FOR USE

(71) Applicant: BLUEFISH ORTHOPEDICS, LLC, Bloomington, IN (US)

(72) Inventors: Andrew K. Palmer, Eastham, MA (US); Dale Dellacqua, Bloomington, IN (US)

(73) Assignee: Bluefish Orthopedics, LLC, Bloomington, IN (US)

( * ) Notice: Subject to any disclaimer, the term of this patent is extended or adjusted under 35 U.S.C. 154(b) by 0 days.

(21) Appl. No.: 14/157,182

(22) Filed: Jan. 16, 2014

(65) Prior Publication Data

US 2014/0135937 A1     May 15, 2014

Related U.S. Application Data

(62) Division of application No. 13/219,008, filed on Aug. 26, 2011, now Pat. No. 8,647,388.

(60) Provisional application No. 61/377,511, filed on Aug. 27, 2010.

(51) Int. Cl.
    *A61F 2/38*     (2006.01)
    *A61F 2/30*     (2006.01)

(52) U.S. Cl.
    CPC ..... *A61F 2/3804* (2013.01); *A61F 2002/30604* (2013.01); *A61F 2002/3813* (2013.01)

(58) Field of Classification Search
    CPC .................................................. A61F 2/3804
    USPC ........................................... 623/20.11–20.13
    See application file for complete search history.

(56) References Cited

U.S. PATENT DOCUMENTS

| | | | |
|---|---|---|---|
| 3,760,427 A | 9/1973 | Schultz | |
| 3,990,118 A | 11/1976 | Strickland et al. | |
| 4,293,963 A | 10/1981 | Gold et al. | |
| 5,376,121 A | 12/1994 | Huene et al. | |
| 5,782,923 A | 7/1998 | Engelbrecht et al. | |
| 5,879,395 A | 3/1999 | Tornier et al. | |
| 6,027,534 A | 2/2000 | Wack et al. | |
| 6,379,387 B1 | 4/2002 | Tornier | |
| 6,699,290 B1 | 3/2004 | Wack et al. | |
| 6,875,236 B2 * | 4/2005 | Reiley | 623/21.18 |
| 7,247,170 B2 | 7/2007 | Graham et al. | |
| 7,449,028 B2 | 11/2008 | Ball | |
| 7,507,256 B2 | 3/2009 | Heck et al. | |
| 7,850,737 B2 | 12/2010 | Morrey | |
| 2004/0122440 A1* | 6/2004 | Daniels et al. | 606/102 |
| 2010/0222887 A1* | 9/2010 | Katrana et al. | 623/20.11 |
| 2011/0153024 A1 | 6/2011 | Wagner et al. | |

* cited by examiner

*Primary Examiner* — Thomas J Sweet
*Assistant Examiner* — Brian Dukert
(74) *Attorney, Agent, or Firm* — Brennan, Manna & Diamond, LLC

(57) ABSTRACT

The elbow prosthesis includes an ulnar component that has a bearing end and a stem. The stem is attached to the bearing end and extends in a distal direction from it. The elbow prosthesis also has a humeral component that includes a holder end and a stem with the stem extending in a proximal direction from the holder end. The prosthesis further includes at least one bearing member that is connected to the holder end with the bearing end being attached within the holder end to allow for rotation and articulation against the at least one bearing member. The bearing end and holder end are attached to each other by a coupling mechanism that includes an opening positioned on the posterior aspect of the holder end and a mating surface on the bearing body. A method of using the elbow prosthesis and a total elbow prosthesis kit are also disclosed.

24 Claims, 15 Drawing Sheets

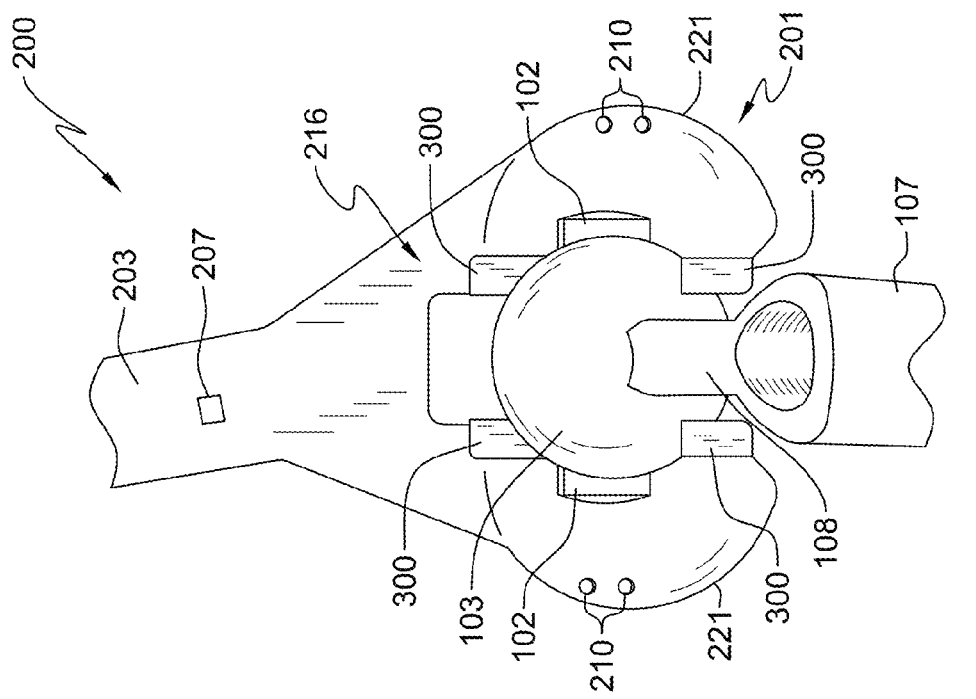
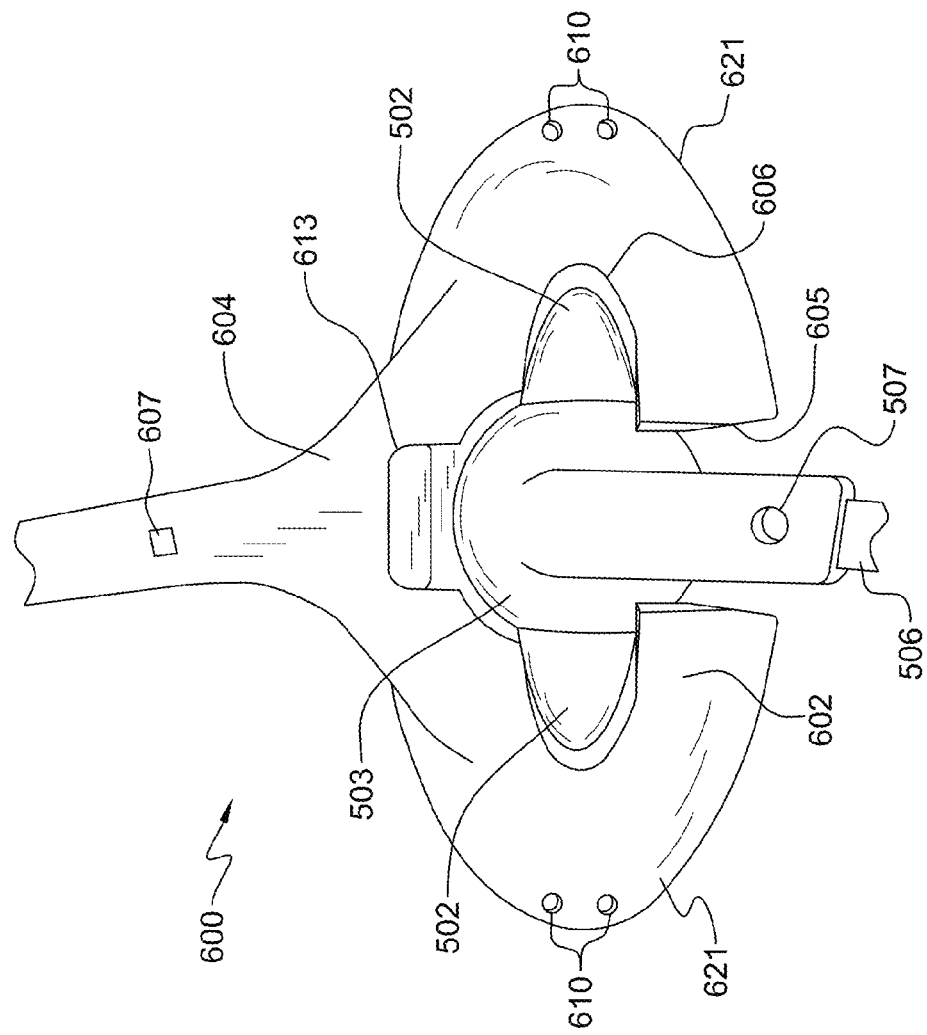
FIG. 10

ELBOW PROSTHESIS AND METHOD FOR USE

CROSS-REFERENCE TO RELATED APPLICATION

This application is a divisional of U.S. application Ser. No. 13/219,008 filed Aug. 26, 2011, which claims priority to U.S. Provisional Application No. 61/377,511 filed Aug. 27, 2010, each of which are hereby incorporated herein by reference in their entireties.

TECHNICAL FIELD

The present invention relates generally to the field of orthopedics and more specifically, but not exclusively, to artificial joints, and in particular, to an elbow joint prosthesis.

BACKGROUND OF THE INVENTION

In the human elbow, three degrees of freedom are present. These are flexion-extension, varus-valgus carrying angle and axial rotation.

The various elbow prosthesis available in the marketplace today have been constructed as a replacement for the natural human elbow. The two basic types of elbow prosthesis known in the prior art are semi-constrained and unconstrained. In semi-constrained prosthesis, the prosthetic joint is held together mechanically, by components of the prosthesis. Whereas in an unconstrained device, the prosthetic device is held together by the patient's natural soft tissues.

In each of these devices, one portion of the prosthesis is implanted in the humerus of the patient and the other portion is implanted in the ulna. The two portions then mate in some manner to allow articulation of the joint. Importantly, absent from the marketplace is a device that can be implanted when either the humerus or ulna and/or both bones are compromised either from disease or injury.

Prosthetic elbows currently marketed typically can be implanted to operate in one of two ways. These two ways are an unconstrained or unlinked manner and the other way is a semi-constrained or linked manner. Unconstrained prosthetic elbows are more generally indicated for osteoarthritic or post traumatic patients with strong soft tissues about the elbow.

Typically, unconstrained elbows are designed with, for example, a metal humeral articulating surface and a polyethylene ulnar articulating surface. Each of these components having matching convex and concave surfaces, respectively.

The semi-constrained prosthesis is usually used in patients that are suffering from an inflammatory disease. The inflammatory disease results in the patient having weaker soft tissue and significant bone erosion. The weaker soft tissue and bone erosion makes the use of an unconstrained elbow more difficult in that the soft tissues are not of sufficient strength to properly contain the prosthetic components in contact with each other. A semi-constrained prosthesis typically uses a linkage pin at the elbow axis of rotation. Most commercially available elbow devices make use of a locking axis pin as the main element of articulation for the semi-constrained form of the elbow prosthesis.

A long standing need has existed for the orthopedic surgeon to have available an elbow prosthesis that addresses the clinical problems that result from a post-traumatic injury to the elbow. More specifically, currently no elbow implant designs exist that are specifically indicated for use to treat complex fractures of the distal humerus and/or proximal ulna.

Please note that for the purposes of this disclosure, the terms "prosthesis," "implant" and "device" may be used interchangeably and have the same meaning herein.

SUMMARY OF THE INVENTION

Advancement of the state of total elbow arthroplasty and the surgical management relating to the clinical presentation of complex trauma to the elbow is believed desirable. Aspects of the present invention provide for a modular and versatile elbow prosthesis, methods for use that can solve the long-standing need for treatment of traumatic injuries to elbows and a surgical kit that contains numerous sizes of the modular components of the elbow prosthesis.

The present invention provides in one aspect an elbow prosthesis having an ulnar component with a bearing end and a distally extending stem that is coupled to the bearing end. The prosthesis also has a humeral component which includes a holder end and a proximally extending stem with at least one bearing member that is coupled to the holder end. The bearing end is configured to be rotatably coupled within the holder end and articulate against the at least one bearing member.

The present invention provides in another aspect, a method for using the elbow prosthesis. The method may include the step of obtaining an elbow prosthesis that includes an ulnar component having a bearing end and a distally directed stem. The prosthesis may also include a humeral component that has a holder end and stem that extends in a proximal direction and at least one bearing member that is attached to the holder end. The method may further include the step of making an incision in the patient and dissecting the surrounding soft tissue from the elbow joint. An additional step may be to determine the proper size for the ulnar component and the humeral component. Another step may be to cut and prepare the ulna and the humerus. Further steps may be to secure the humeral component into the humerus of the patient and couple the ulnar component to the implanted humeral component resulting in the bearing end of the ulnar component being operatively associated with the holder end of the humeral component to allow movement between the ulnar component and the humeral component. The method may also include inserting and securing the ulnar component in the ulna. Finally, the method may have the step of closing the incision in the patient.

The present invention provides in another aspect, a total elbow prosthesis kit that includes a plurality of humeral components with each of the humeral components having a holder end and a stem extending in a proximal direction. The kit also includes a plurality of ulnar components with the ulnar components having a bearing end and a modular distal stem attached to the bearing end or an ulnar component that has a fixed stem that is attached to the bearing end. The kit also includes a plurality of interchangeable bearing members for fixation to the holder end.

The present invention provides in a further aspect, a semi-constrained total elbow prosthesis that includes an ulnar component having a bearing end and a stem with the stem being coupled to the bearing end and extending in a distal direction from the bearing end. The prosthesis also has a humeral component that has a housing member and a proximally extending fixed stem. The semi-constrained elbow prosthesis may also have at least one bearing member that is coupled to an inside surface of the housing member. The bearing end is configured to be inserted into the housing member and articulate against the at least one bearing member to allow for motion between the ulnar component and humeral component.

The present invention in yet another aspect, a total elbow prosthesis having an ulnar component with a bearing end and a modular stem that is configured to fit inside a bone. The prosthesis also has a humeral component that includes a stem and a distal yoke with the yoke terminating in a pair of spaced apart arms that each have a distal bearing holder member. At least two bearing members are also included in the prosthesis with the at least two bearing members being attached to an inner surface of each of the bearing holder members. The prosthesis has a coupling mechanism that is positioned between the pair of spaced apart arms and functions to attach the ulnar component to the humeral component and allow the ulnar component to rotate relative to the humeral component along the sagittal plane.

Details of these aspects of the invention, as well as further, additional features and advantages will become more readily apparent upon review of the following drawings and claims. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention will be readily understood from the following detailed description taken in conjunction with the accompanying drawings in which:

FIG. 10 is a posterior view of two embodiments of a total elbow prosthesis showing the extended medial and lateral aspects of the holder end of the humeral component, in accordance with an aspect of the present invention;

DETAILED DESCRIPTION FOR CARRYING OUT THE INVENTION

Disclosed herein is a total elbow prosthesis, a corresponding surgical implantation method and a total elbow prosthesis kit.

Figure 1:
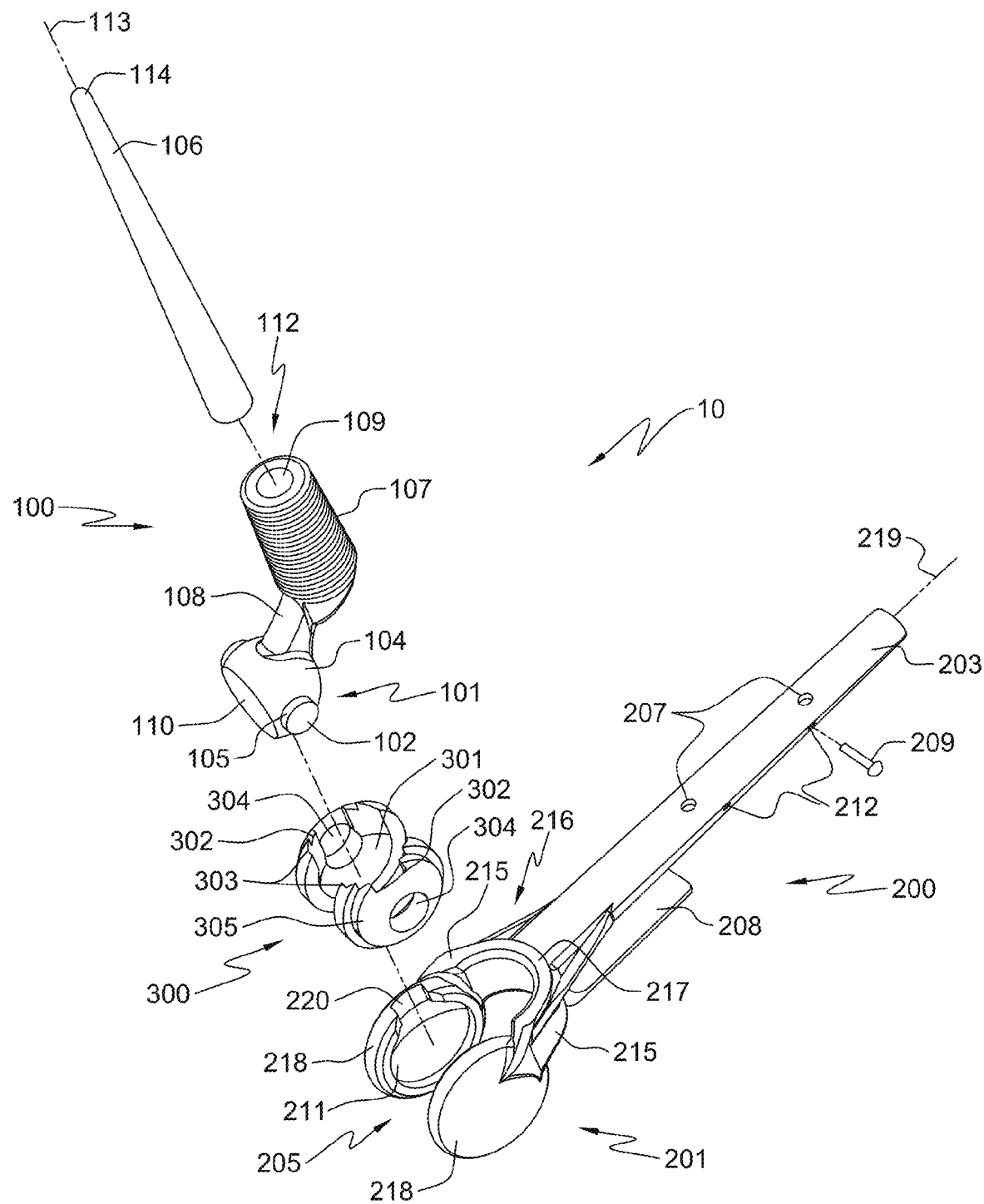
FIG. 1 is an exploded posterior, perspective view of one embodiment of an elbow prosthesis, in accordance with an aspect of the present invention.

FIG. 1 is an exploded posterior view of a first embodiment of a disassembled elbow prosthesis 10 according to one aspect of the invention. Elbow prosthesis 10 includes ulnar component 100 which may include a bearing end 101 that has at least one projection/boss 102 extending for example in the medial and/or lateral directions. As seen, projection 102 may have straight cylindrical side walls 105 to facilitate insertion into the bearing member 300. Alternatively, side walls 105 may be tapered. The surface of side walls 105 is configured to mate and articulate with bearing member 300 and function as a means of aligning ulnar component 100 relative to the humeral component 200. Bearing end 101 of ulnar component also includes a centralized bearing body 103 that as seen may have a spherical-like shaped outer bearing surface 104. Body bearing surface 104 is convex or has an arcuate shape to facilitate rotational movement of ulnar component 100 relative to humeral component 200 that mimics the natural elbow motion when these components are rotatably coupled. Bearing body 103 is comprised of body bearing surface 104 and a mating surface 110.

As shown in FIG. 1, mating surface 110 is, for example, planar or flat, although it would be understood by one skilled in the art that other geometric configurations could be used. As described below in more detail, mating surface 110 is a component of the coupling mechanism 111. (See FIG. 5).

Figure 4:
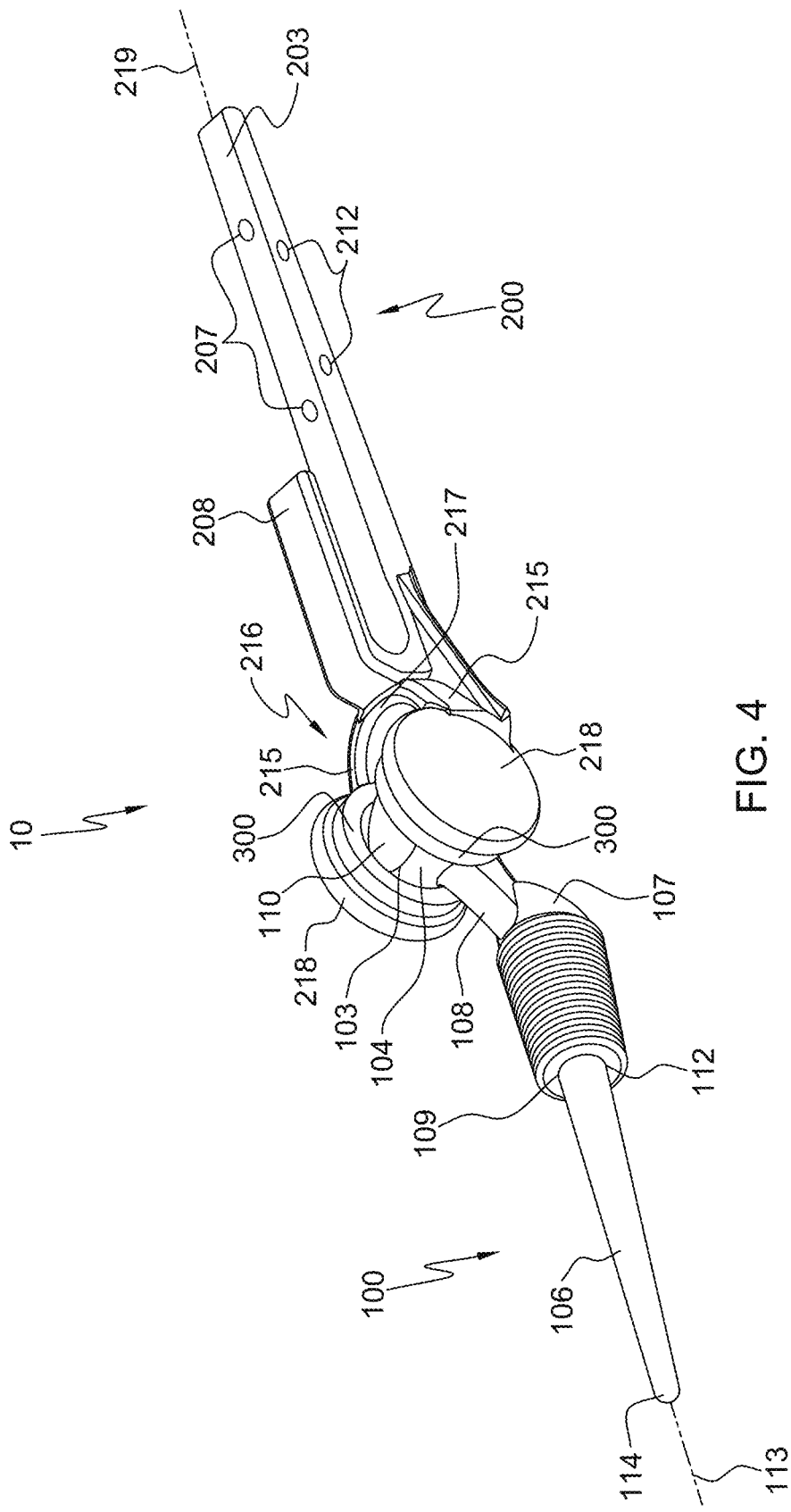
FIG. 4 is an anterior, perspective view of the elbow prosthesis of FIG. 1, in accordance with an aspect of the present invention.

FIGS. 1 and 4 also show bearing end 101 including an offset neck 108 that facilitates the replication of the mechanical and anatomical orientation of elbow prosthesis 10 following implantation in the body. Neck 108 extends at an acute angle from the inferior aspect of body bearing surface 104 and terminates at the stem connector member 107. Stem connector member 107 has a generally cylindrical cross-sectional geometry, although, alternatively, other polygonal cross-sectional geometric shapes may be used. The outer surface of stem connector member 107 may be macrotextured, have a porous coated surface or include a bone growth surface coating, including for example TCP or HA. Stem connector 107 is one aspect of the connecting mechanism 112 that also includes the proximal end of stem 106. Specifically, stem connector 107 includes a connecting hole 109 that may be tapered or have a cylindrical internal shape to mate with an end of stem 106.

Ulnar component 100 also may include a distal projecting modular stem 106 that may be attached to stem connector 107. Stem 106 will extend in a generally distal direction from stem connector 107 after stem 106 has been inserted into connecting hole 109. It would be understood by one skilled in the art that several connecting mechanisms 111 could be used to connect the end of stem 106 to stem connector 107, including but not limited to a morse taper, press-fit, a locking pin and a swag joint. Although not shown, an alternative embodiment of ulnar component 100 may include stem 106 being integrally fixed to stem connector member 107.

As shown in FIGS. 1, 2, 3 and 4, stem 106 may be tapered to facilitate insertion into the intramedullary canal of a bone. Alternatively, although not shown, stem 106 may be cylindrically shaped, include a curve or be matched anatomically with the intramedullary canal of the patient into which device is being implanted.

Figure 2:
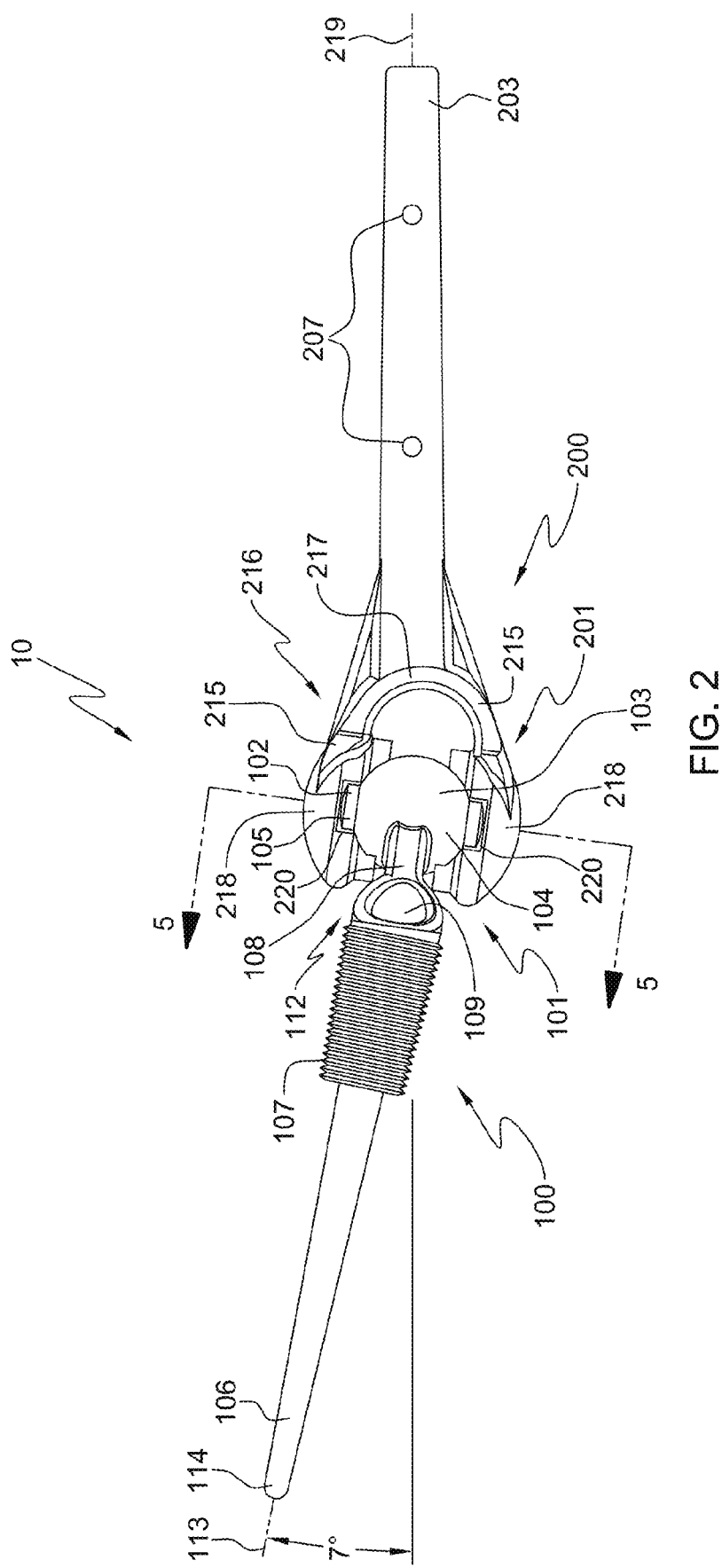
FIG. 2 is a posterior, elevational view of the elbow prosthesis of FIG. 1, in accordance with an aspect of the present invention.
Figure 3:
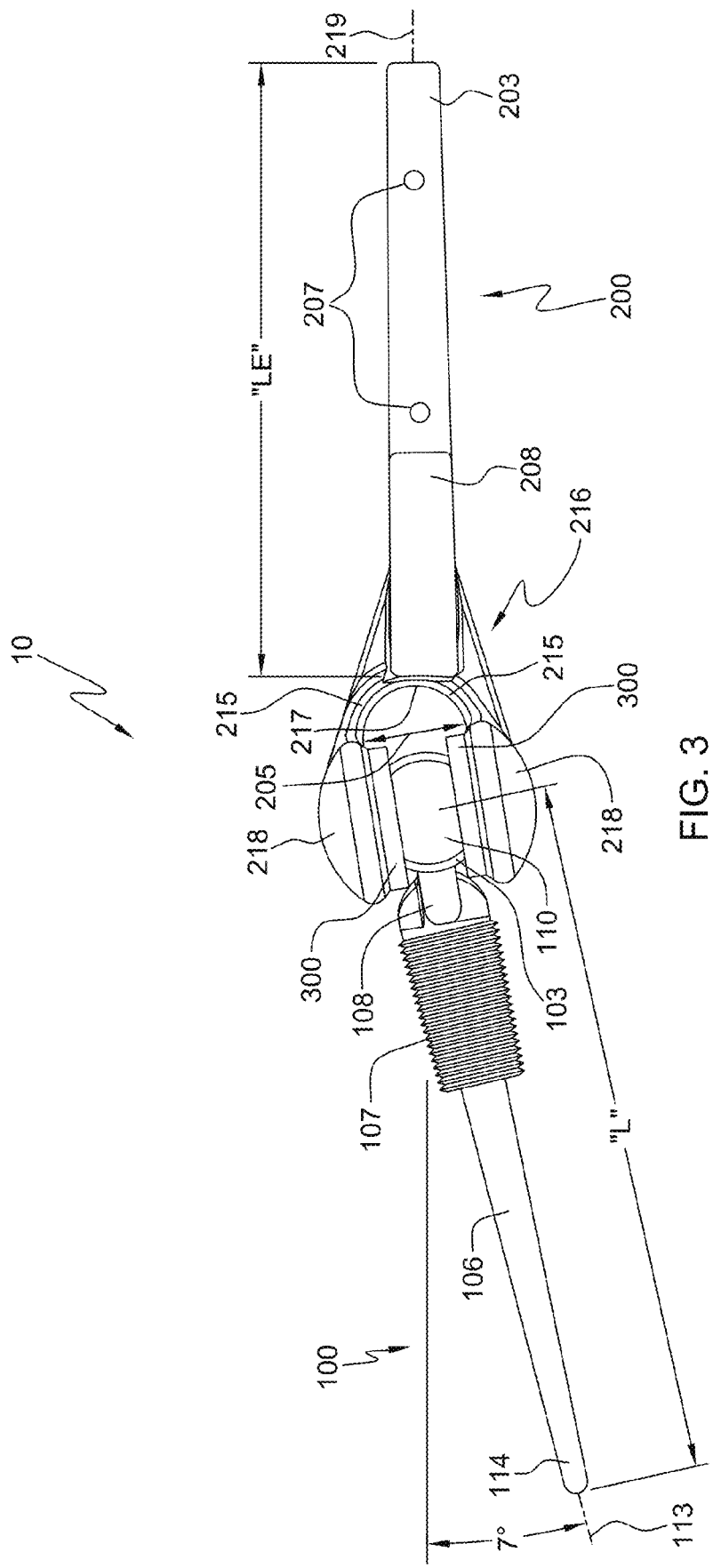
FIG. 3 is a anterior, elevational of the elbow prosthesis of FIG. 1, in accordance with an aspect of the present invention.

As seen in FIGS. 2 and 3, longitudinal axis 113 of stem 106 is angled laterally (valgus) ranging approximately between five and eight degrees, with a preferred range of between 6 and 7 degrees.

Figure 13:
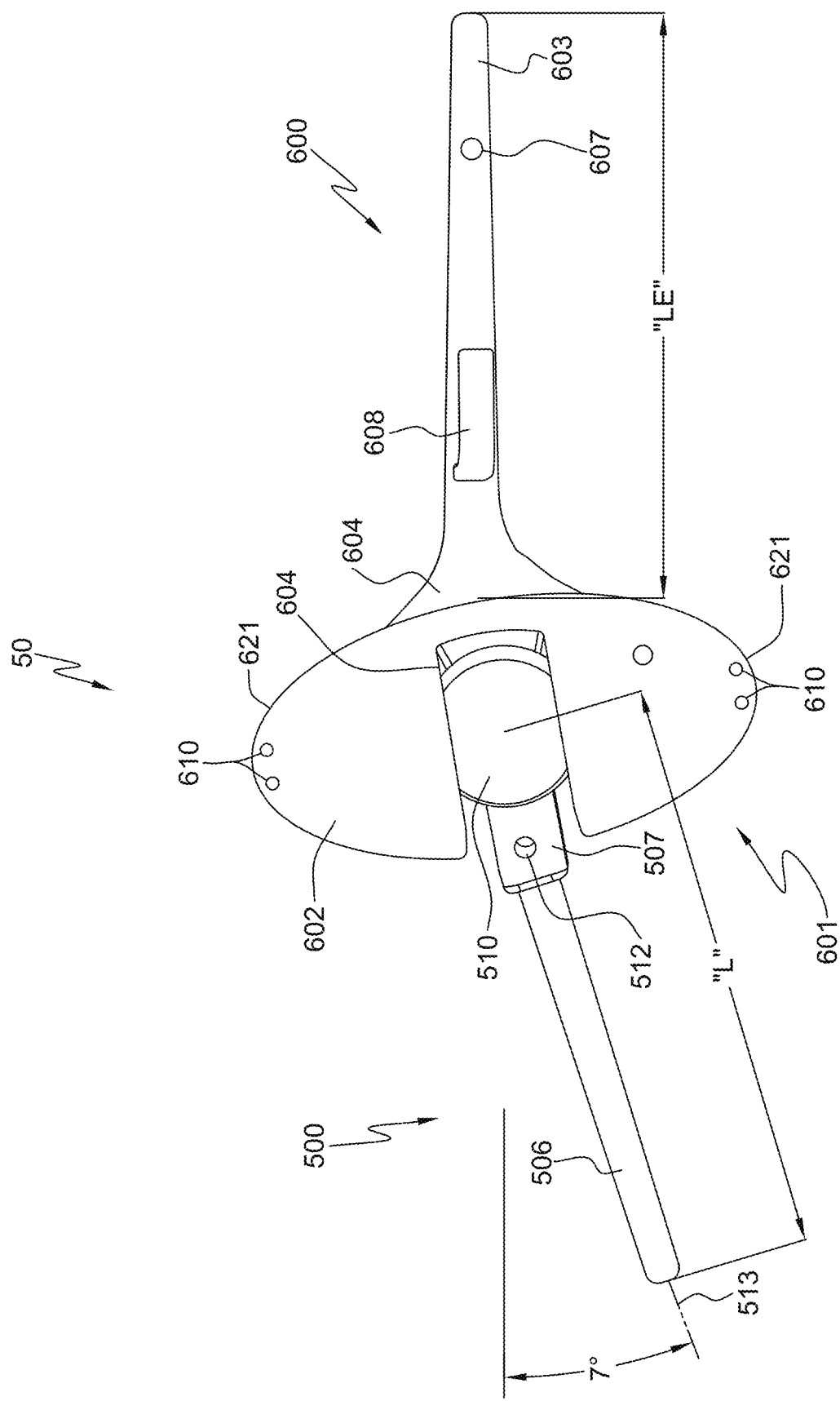
FIG. 13 is an anterior, elevational of the elbow prosthesis of FIG. 11, in accordance with an aspect of the present invention.

As shown in FIGS. 9A-9F, for both embodiments of elbow prosthesis 10, 50, stems 106, 506 and the stem for the humeral component 203, 603 may have various polygonal cross-sectional geometries and sizes for each of the geometries. For example purposes, dimension "A" (for all geometries) may range between 2 and 14 mm, with a preferred range of 3-12 mm for stem 106, 506 while for stem 203, 603 the range may be 3-18 mm with a preferred range of 4-16 mm. Dimension "B" (for all geometries) for stem 106, 505 may be between 2-14 mm, with a preferred range of 3-12 mm. For stem 203, 603 the range may be between 2-16 mm, with a preferred range of 3-14 mm. As seen in FIGS. 3 and 13, the overall lengths "L" of stems 106, 506 as measured from the center of rotation of the humeral holder end 201 to the tip 114, 514 will range between 35-150 mm, with a preferred range of 40-125 mm. For stem 203, 603, the length "LE" may be between 60-150, with a preferred range of 75-125 mm. Further, the surfaces of stems 106, 506, 203, 603 may have various coatings or treatment applied to them, including, but not limited to porous coating, bead blasting, generated integral nanosurfaces, HA coatings, TCP coatings, BMP coatings and other well know bone growth facilitating agents or substrate coatings.

Figure 11:
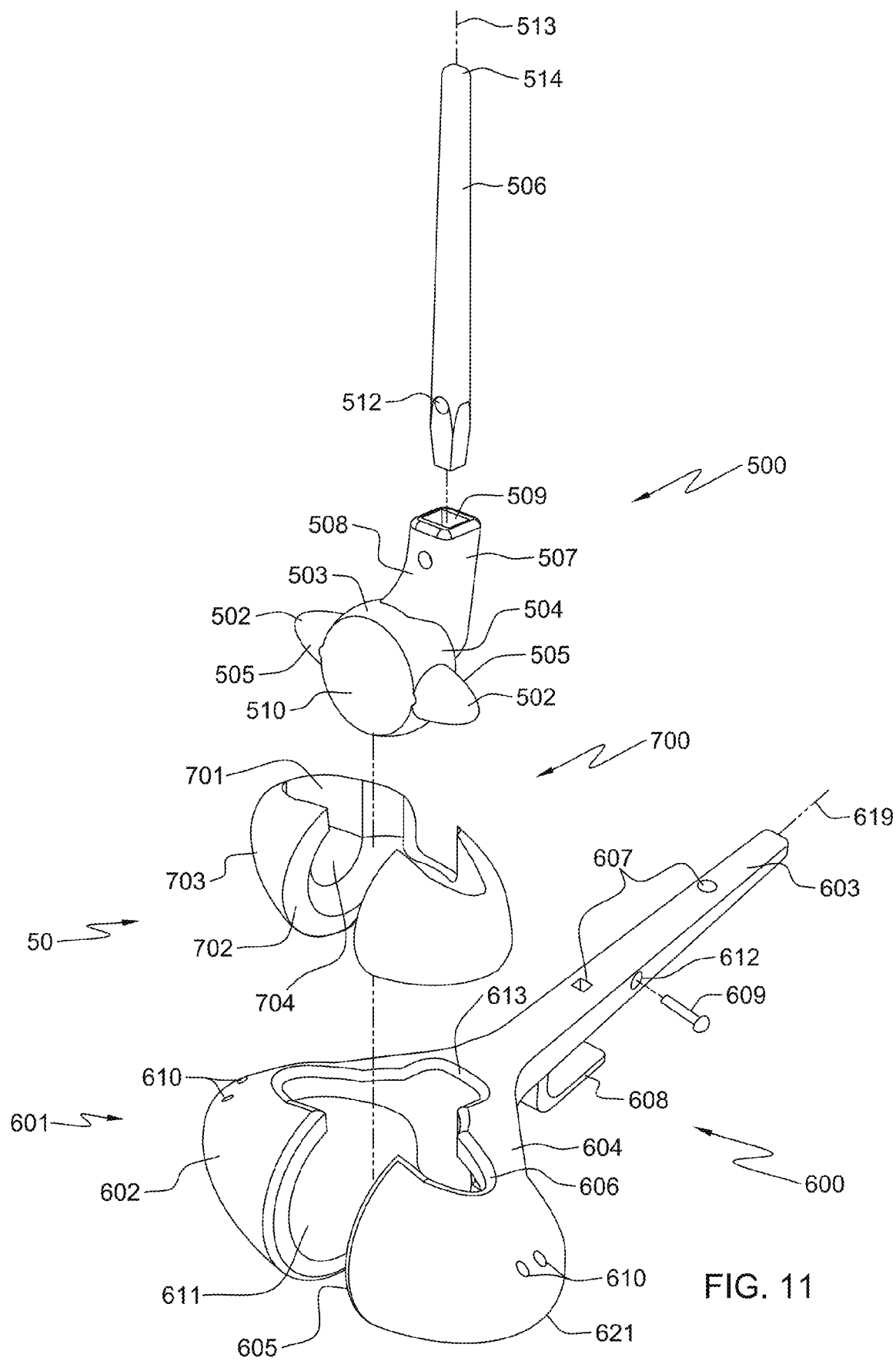
FIG. 11 is an exploded posterior, perspective view of another embodiment of an elbow prosthesis, in accordance with an aspect of the present invention.

As seen in FIGS. 1 and 11, stem 203, 603 may also be configured to accommodate transverse fixation devices 209, 609, including screws, posts and pins. These transverse fixation devices 209, 609 may be directed through bone on one side of the stem 203, 603 then enter hole 212, 612 pass all the way through stem 203, 603 and exit into adjacent bone on the opposite side to provide immediate stability to implant 10, 50. The fixation devices 209, 609 may be positioned in the medial-lateral or anterior-posterior direction.

Ulnar component 100 may be constructed from various biocompatible materials including metals (e.g., titanium, cobalt chromium), composites (PEEK), polymers (UHMWPE, Delrin) or elastomers, as well as combinations of these materials.

Figure 6A:
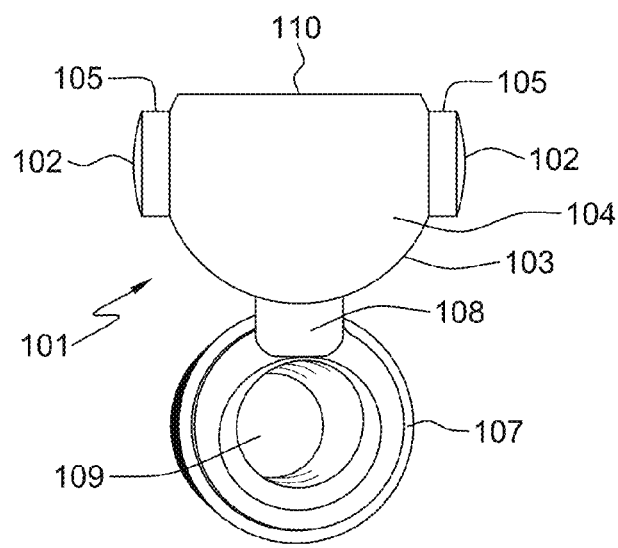
FIG. 6A is a posterior view of one embodiment of a spherical shaped bearing body of a bearing end of the elbow prosthesis in FIG. 1, in accordance with an aspect of the present invention.
Figure 6B:
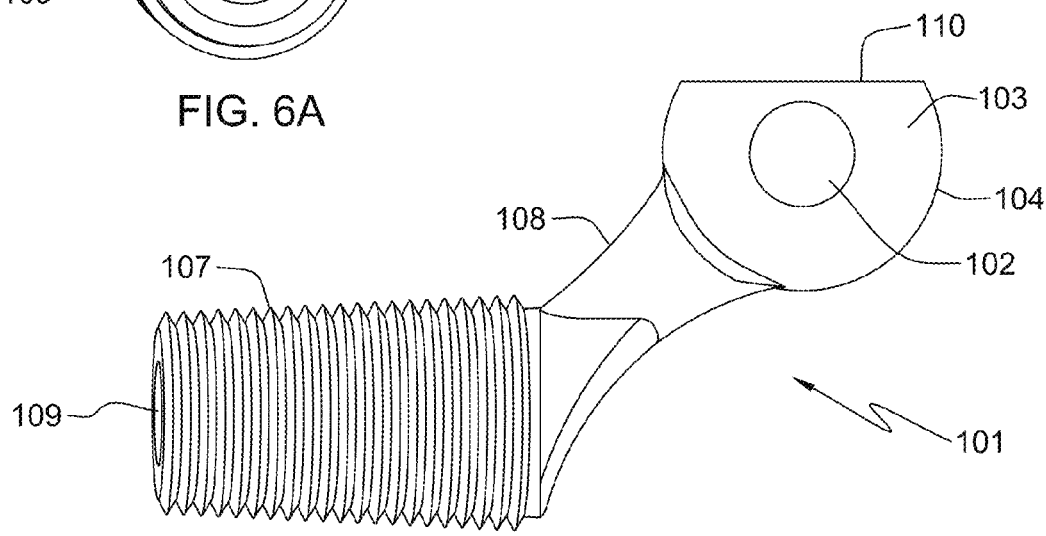
FIG. 6B is a lateral view of one embodiment of a spherical shaped bearing body of a bearing end of the elbow prosthesis in FIG. 1, in accordance with an aspect of the present invention.
Figure 6C:
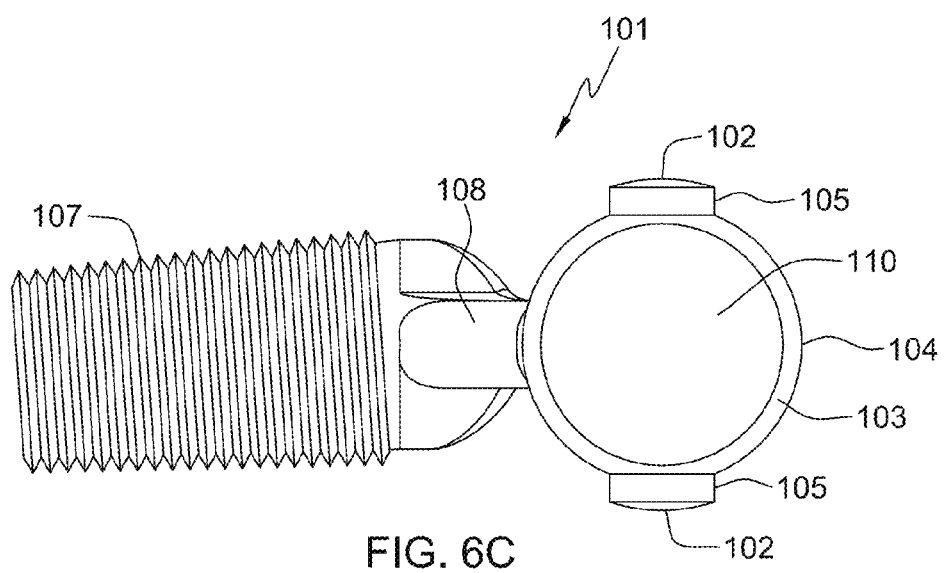
FIG. 6C is a superior view of one embodiment of a spherical shaped bearing body of a bearing end of the elbow prosthesis in FIG. 1, in accordance with an aspect of the present invention.

FIGS. 6A-6C show one alternative embodiment of the configuration of bearing end 101 and more specifically, the shape of centralized bearing body 103. FIG. 6A is a posterior view of a spherical shaped bearing body 103 that includes medial and lateral projections 102 and mating surface 110. FIG. 6B is a lateral elevational view of bearing end 101 of FIG. 6A and shows neck 108 extending from the inferior aspect of bearing body 103 that connects to stem connector member 107. FIG. 6C is a superior view of the bearing end 101 of FIG. 6A that shows mating surface 110. As seen in all of these figures, stem connector member 107 includes a macro-textured surface.

Figure 7A:
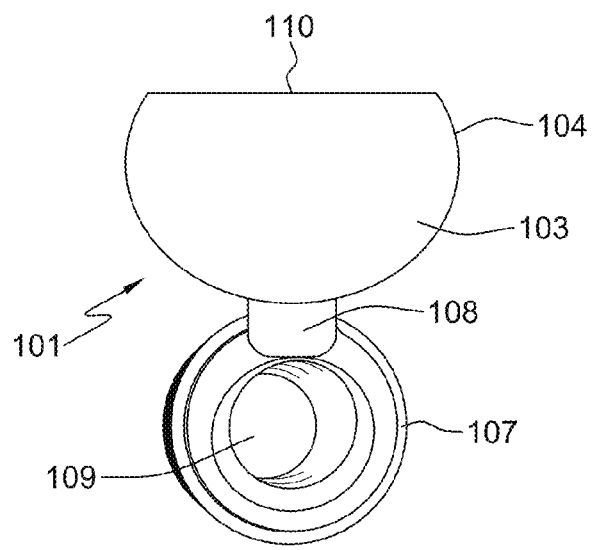
FIG. 7A is a posterior view of one embodiment of an elliptical shaped bearing body of a bearing end of the elbow prosthesis in FIG. 1, in accordance with an aspect of the present invention.
Figure 7B:
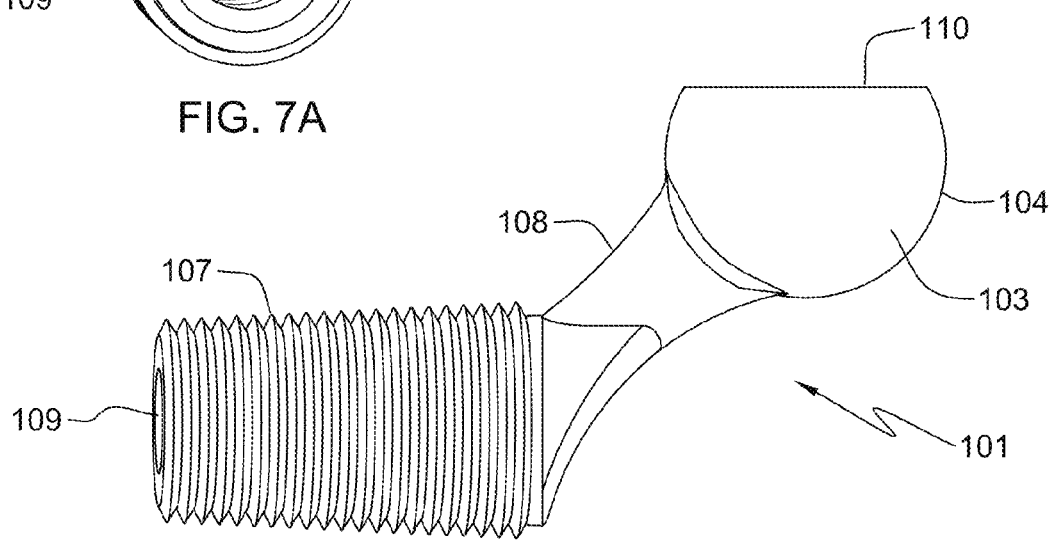
FIG. 7B is a lateral view of one embodiment of an elliptical shaped bearing body of a bearing end of the elbow prosthesis in FIG. 1, in accordance with an aspect of the present invention.
Figure 7C:
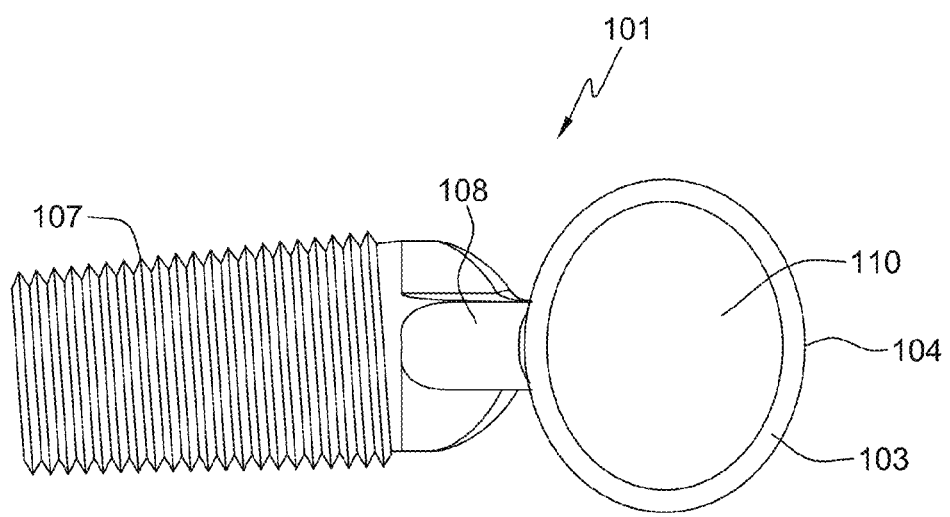
FIG. 7C is a superior view of one embodiment of an elliptical shaped bearing body of a bearing end of the elbow prosthesis in FIG. 1, in accordance with an aspect of the present invention.

FIGS. 7A-7C show a second alternative embodiment of the configuration of bearing end 101 and more specifically, the shape of centralized bearing body 103 is seen as an elliptical-like shape in the transverse plane. FIG. 7A is a posterior view of the elliptical shaped bearing body 103 that includes mating surface 110. FIG. 7B is a lateral elevational view of the bearing end 101 of FIG. 7A showing neck 108 extending from the inferior aspect of bearing body 103 to connect with stem connector member 107. FIG. 7C is a superior view of the bearing end 101 of FIG. 7A that shows the elliptical shaped mating surface 110. As seen in all of these figures, stem connector member 107 includes a macro-textured surface.

Figure 8A:
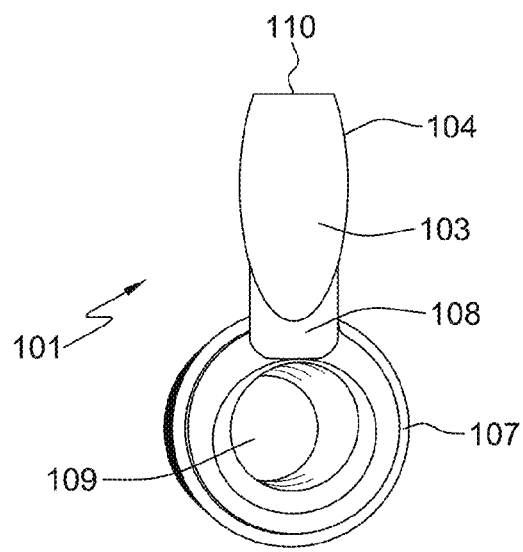
FIG. 8A is a posterior view of one embodiment of an oval shaped bearing body of a bearing end of the elbow prosthesis in FIG. 1, in accordance with an aspect of the present invention.
Figure 8B:
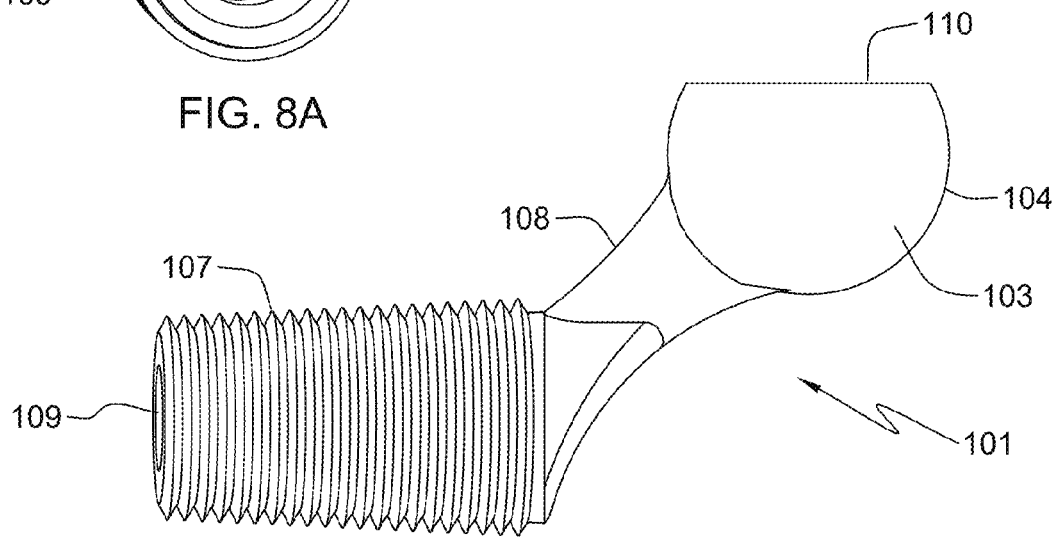
FIG. 8B is a lateral view of one embodiment of an oval shaped bearing body of a bearing end of the elbow prosthesis in FIG. 1, in accordance with an aspect of the present invention.
Figure 8C:
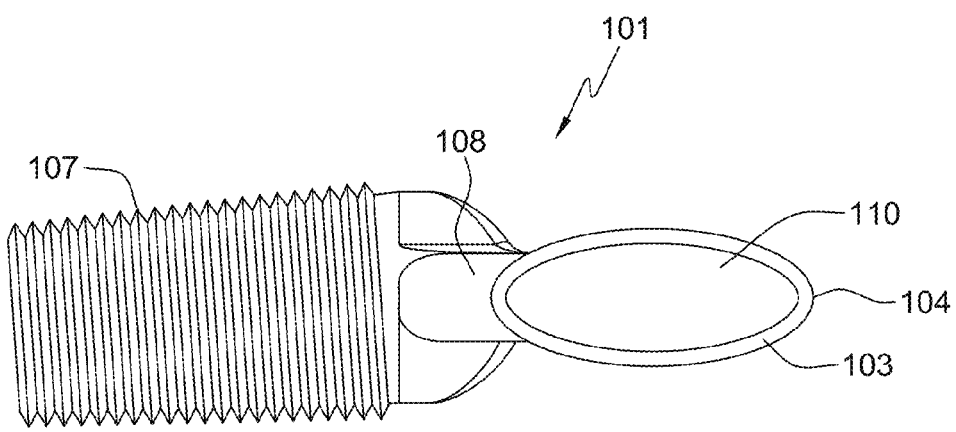
FIG. 8C is a superior view of one embodiment of an oval shaped bearing body of a bearing end of the elbow prosthesis in FIG. 1, in accordance with an aspect of the present invention.
Figure 9F:
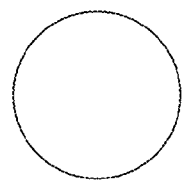
FIG. 9F is a cross-sectional view of one embodiment of the ulnar stem or humeral stem having a quatrefoil shape, in accordance with an aspect of the present invention.
Figure 9E:
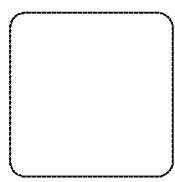
FIG. 9E is a cross-sectional view of one embodiment of the ulnar stem or humeral stem having an elliptical shape, in accordance with an aspect of the present invention.
Figure 9D:
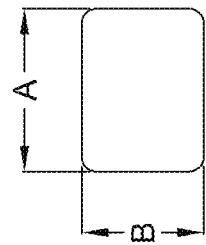
FIG. 9D is a cross-sectional view of one embodiment of the ulnar stem or humeral stem having a trapezoidal shape, in accordance with an aspect of the present invention.
Figure 9C:
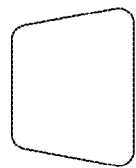
FIG. 9C is a cross-sectional view of one embodiment of the ulnar stem or humeral stem having a rectangular or oblong shape, in accordance with an aspect of the present invention.
Figure 9B:
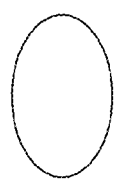
FIG. 9B is a cross-sectional view of one embodiment of the ulnar stem or humeral stem having a square shape, in accordance with an aspect of the present invention.
Figure 9A:
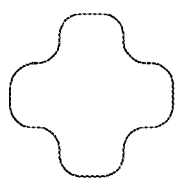
FIG. 9A is a circular cross-sectional view of one embodiment of the ulnar stem or humeral stem having a circular shape, in accordance with an aspect of the present invention.

FIGS. 8A-8C show a third alternative embodiment of the configuration of bearing end 101 and more specifically, the shape of centralized bearing body 103 is seen as an oval-like shape in the transverse plane. FIG. 8A is a posterior view of the oval shaped bearing body 103 that includes mating surface 110. FIG. 8B is a lateral elevational view of the bearing end 101 of FIG. 8A showing neck 108 extending from the inferior aspect of bearing body 103 to connect with stem connector member 107. FIG. 7C is a superior view of the bearing end 101 of FIG. 8A that shows the oval shaped mating surface 110. As seen in all of these figures, stem connector member 107 includes a macro-textured surface.

FIGS. 1-4 further show in addition to ulnar component 100, humeral component 200. Humeral component 200 includes a holder end 201 with a proximal extending stem 203. Holder end 201 is configured to generally have a yoke-like shape 216 with two arms 215 extending distally from the arch 217.

Coupled to the distal end of arms 215 is a bearing holder member 218 that has an inner surface 211 to which bearing member 300 is attached. The mechanism of attachment of bearing member 300 to inner surface 211 may include a snap lock, press fit or other similar design. Each bearing holder member 218 also includes a posterior directed notch 220 through which bearing member 300 may slide during assembly of implant 10 to ensure proper orientation of bearing member 300 relative to bearing holder 218 (see FIG. 2). Arms 215 are spaced apart at a set distance 205 to accommodate bearing members 300 and the coupled bearing end 101 of ulnar component 100.

As seen in FIG. 4, positioned adjacent to arch 217 of yoke 216 is a flange 208. The opening of flange 208 is directed superiorly to allow for the capture of tissue or bone when stem 203 is slid into the intramedullary canal of the humerus during implantation. Flange 208 is integrally fixed to the anterior surface of stem 203, although it is contemplated that flange 208 may be removable be positioned at various positions along the shaft of stem 203. As shown in FIG. 4, stem 203 may include several holes 207 spaced apart along both the anterior and posterior (not shown) surfaces to accommodate modular flanges. The modular flanges may be secured into holes 207 at various locations to address clinical circumstance and stabilize humeral component 200 within the bone. Additional stabilization may also be achieved by inserting a screw or other bone fixation device 209 transverse to longitudinal axis 219 through holes 212. (See FIG. 1). The use of screws or other bone fixation devices 209 will be dependent upon the quality of bone and the clinical situation presented.

As shown in FIG. 1, stem 203 is fixed to holder end 201, although alternatively, stem 203 may be modular and be secured in a similar manner as is used for stem 106 of ulnar component 100 that has been described above. Additionally, for the embodiment of humeral component 200 that includes a modular stem, the stem may be tapered to facilitate insertion into the intramedullary canal of a bone or alternatively, be cylindrically shaped, include a curve or be matched anatomically with the intramedullary canal of the patient into which humeral component 200 is being implanted.

FIG. 1 further shows bearing member 300 that has an articulating surface 301, a posterior directed slot 302, with a top surface or shelf 303. Articulating surface 301 is concave in shape to accommodate projections 102 and bearing surface 104. Positioned generally at the apex of the concavity of articulating surface 301 is an opening 304 to receive projections 102 and secure proper alignment between articulating surface 301 and the bearing surfaces of projections 102 and bearing body 103. The outer surface 305 is configured in a manner that allows for secure attachment to inner surface 211 of bearing holder 218. Securement of bearing member 300 to bearing holder 218 may be achieve using a press-fit, snap lock or other similar mechanism.

Figure 5:
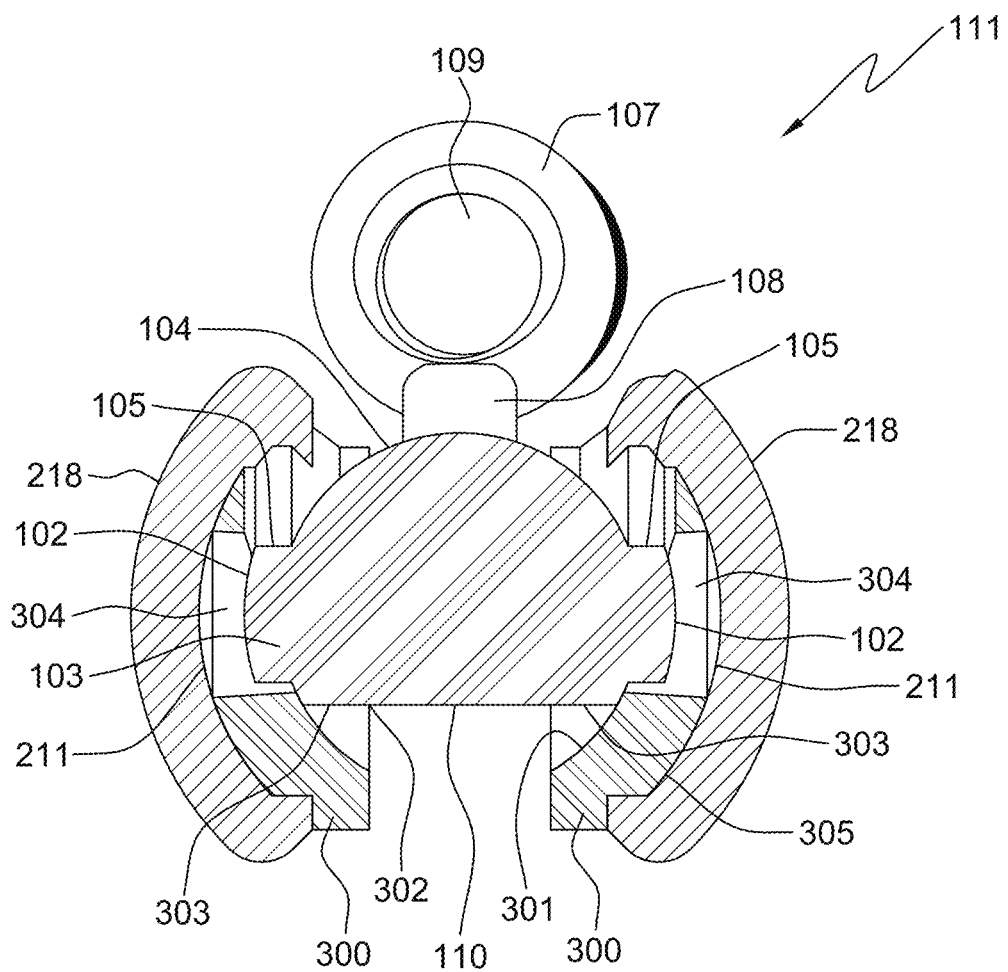
FIG. 5 is cross-sectional-view taken along line 5-5 in FIG. 2, showing the coupling mechanism between the ulnar component and the humeral component of the elbow prosthesis of FIG. 1, in accordance with an aspect of the present invention.

FIG. 5 is a cross-sectional view through the assembled implant 10 showing coupling mechanism 111. Specifically, the sectional view shows centralized bearing body 103 inserted between bearing holders 218 and articulating with bearing member 300 to comprise coupling mechanism 111. Also seen in FIG. 5 are projections 102 extending into the lateral openings 304 of bearing member 300. Bearing surface 104 slides along articulation surface 301 when the prosthesis moves through a range of motion. An outer surface 305 of bearing member 300 is seen to be adjacent to inner surface 211 of bearing holder 218. Although not shown, inner surface is configured to secure bearing member 300 within the inner portion of bearing holder 218. Securement may be accomplished using a press-fit arrangement, snap-fit or a variable locking mechanism, like a pin or other similar mechanical configuration.

For example purposes, a snap-fit design may be comprised of several circumferentially positioned scallops or depressions disposed on inner surface 211 that are aligned with correspondingly positioned mating protrusions on surface 305. The arrangement of depressions and protrusions will ensure appropriate alignment and securement between bearing member 300 and bearing holder 218.

FIG. 5 depicts the internal arrangement of centralized bearing body 104, bearing member 300 and bearing holder 218, which comprise the coupling mechanism 111 during the coupling process. Externally, the coupling process is accomplished by initially aligning centralized bearing body 103 with the holder end 201, but more specifically for prosthesis 10 this involves aligning mating surface 110 of bearing body 103 with slot 302 and top surface of slot 303 of bearing member 300 which is positioned at about ninety degrees of hyperextension of the implant (two hundred and seventy degrees counterclockwise), as well as projections 102 with notches 220. Once aligned, bearing body 103 is slid into slot 302 that is positioned between arms 215 and aligned with notch 220. Mating surface 110 is slid across top surface or shelf of slot 303 while projections 102 slide into slot 303 until projections 102 come to rest within holes 304. This type of arrangement being analogous to a keyed opening. Following the full nesting of centralized bearing head 103 between bearing members 300, ulnar component 100 is then rotated from ninety degrees of hyperextension into extension and then flexion thereby causing mating surface 110 to no longer be aligned with top surface 303 of slot 302 and locking ulnar component 100 and humeral component 200 together, although allowing rotational movement along Line 5-5 of FIG. 2.

FIGS. 11-14 show a second embodiment of the total elbow prosthesis 50. FIG. 11 is an exploded view showing ulnar component 500, bearing member 700 and humeral component 600.

As seen in FIG. 11, ulnar component 500 may include a bearing end 501 that has at least two tapered cylindrical projections 502 extending, for example, in the medial and lateral directions. Each projection 502 has a bearing surface 505 that will contact and articulate with an inner bearing surface 701 positioned within a cavity 611 of humeral housing member 602. The bearing end 501 also has a centralized bearing body 503 that may have a spherical-like shaped outer bearing surface 504. The body bearing surface 504 is curved or has an arcuate shape to facilitate rotational movement of ulnar component 500 relative to humeral component 600, when these elements are coupled together to mimic the natural elbow motion. Also disposed on centralized bearing body 503 is a mating surface 510. For example purposes this is shown as a planar surface, although other distinctly shaped surfaces could be used. Mating surface 510 is part of the coupling mechanism 511 and is configured to function as a key element in that it must be aligned with a corresponding matching surface in humeral component 600 and bearing member 700 to allow mating surface 510 to be slide into inner cavity 611 of humeral component and then connect ulnar component 500 to humeral component 600.

Figure 14:
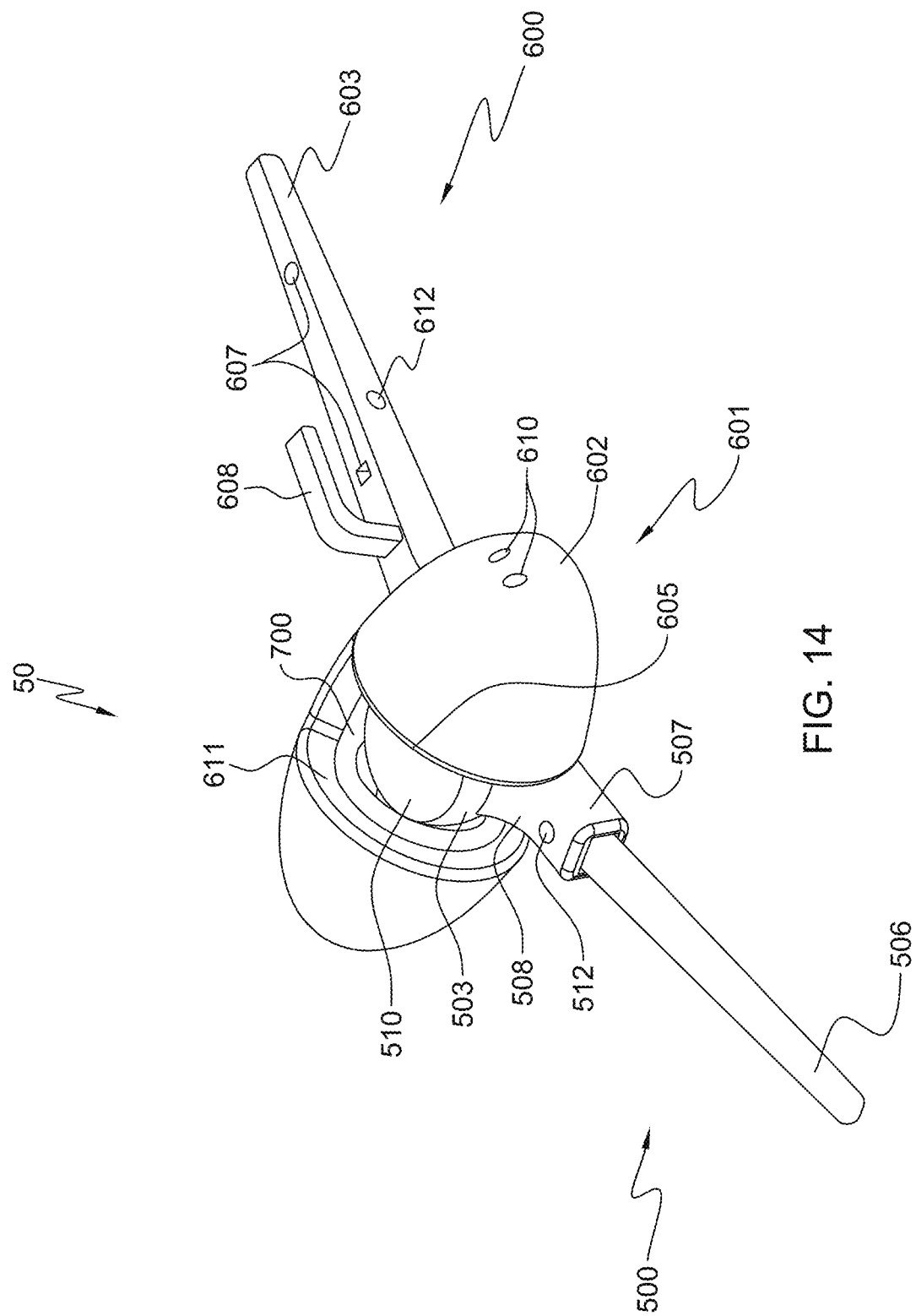
FIG. 14 is an anterior, perspective view of the elbow prosthesis of FIG. 11, in accordance with an aspect of the present invention.

FIGS. 11 and 14 also show a neck 508 extending from the inferior aspect of centralized bearing body 503. Neck 508 connects bearing body 503 with stem connector member 507. As seen, stem connector member 507 has a mating or connecting hole 509 that is sized to receive a corresponding end of the distal extending stem 506.

As seen in FIG. 11, for example purposes, a taper lock is used to attach stem 506 to stem connector member 507, although it would be understood by one skilled in the art that several coupling mechanisms could be used for this function, including but not limited to press-fit, a locking pin or a swag joint. Further, although not shown, stem 506 may also be integrally connected to stem connector member 507. As already discussed above for stem 106, having stem 506 be modular in construct provides many advantages to the surgeon in addressing presented clinical situations. These advantages include being able to mix and match stem 506 because of the availability of various lengths, diameters, shaft curvatures, surface coatings and other structural changes that could be incorporated into a modular stem.

Figure 12:
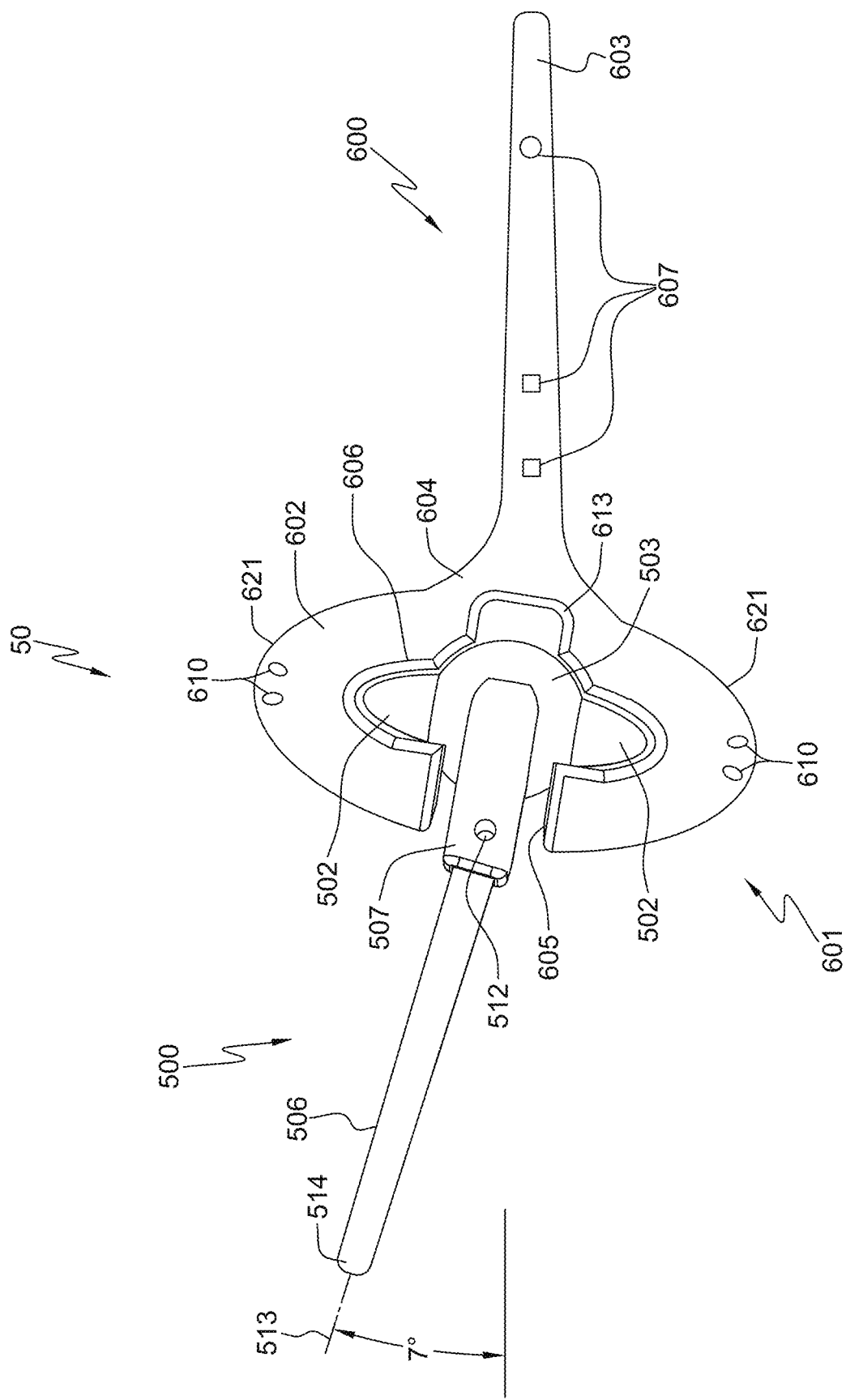
FIG. 12 is a posterior, elevational view of the elbow prosthesis of FIG. 11, in accordance with an aspect of the present invention.

As seen in FIGS. 11, 12 13 and 14, stem 506 is generally straight in the medial-lateral direction, although it could be curved or angled in a medial, lateral, anterior or posterior direction to accommodate a bony deformity. Stem 506 may have a surface coating or treatment applied to it, including porous coating, bead blasting, generated integral nanosurfaces, HA coatings, TCP coatings, BMP coatings and other well known bone growth facilitating agents or substrate coatings. As shown in FIGS. 12 and 13, stem 506 has a valgus angulation of between 5-8 degrees, with a preferred range of between 6 and 7 degrees.

Ulnar component 500 may be constructed from various biocompatible materials including metals (e.g., titanium, cobalt chromium), composites (PEEK), polymers (UHMWPE, Delrin) or elastomers, as well as combinations of these materials.

FIGS. 11, 12, 13 and 14 further exhibit humeral component 600. Humeral component 600 includes a holder end 601 that includes a distal bearing housing member 602. Distal bearing housing member 602 has an inner cavity 611 with a circumferential slot 605 that transects in the sagittal plane, bearing housing member 602.

FIG. 11 shows inner cavity 611 being sized to receive bearing member 700. Bearing member 700 is placed inside inner cavity 611 and is coupled to the inner wall of inner cavity 611 to secure bearing member 700 in position. Such coupling is accomplished using a snap-fit, press-fit or other similar locking mechanism. Bearing member 700 has an inner bearing surface 701 that is shaped to closely approximate and articulate with projection bearing surface 505 and body bearing surface 504. Bearing member 700 also includes a slot 702 that aligns with slot 605 of bearing housing member 602 after insertion into inner cavity 611. Slots 605, 702 are sized to accommodate the width of stem 506 and stem connector member 507 when ulnar component 500 is rotated through a range of motion. Bearing member 700 further includes an outer surface 703 that is positioned adjacent to an inner surface of inner cavity 611 when humeral component 600 is assembled. Bearing member 700 is typically fabricated from UHMWPE, although other bearing materials may be used.

As seen in FIG. 12, opening 606 is positioned on the posterior side of bearing housing member 602. Positioned along the superior edge of opening 606 is a notch 613 to facilitate the insertion of centralized bearing body 503 into inner cavity 611. The combination of opening 606 and notch 613 form a keyed opening that is part of coupling mechanism 511 that is describe further below. Also shown in FIG. 12 is the stem transition area 604 that provides for secure attachment of stem 603 to bearing housing member 602.

FIGS. 11 and 14 further show stem 603 being fixed to bearing housing member 602 and extending in a proximal direction. Stem 603 may be available in various lengths and diameters that will allow the surgeon to customize the elbow prostheses to the clinical situation. These lengths and cross-sectional geometries with dimension have been discussed above and are shown in FIGS. 9A-9F. Although the examples shown provide for stem 603 to be integrally connect to bearing housing member 602, it is understood that stem 603 may also be modular in design, wherein it can be detached from bearing housing member 602 or transition area 604 to allow for customization of stem size, length, curvature and surface coatings to address the large array of clinical issue that may be presented to the operating surgeon.

Stem 603 is also configured to facilitate fixation to the humerus of the patient. This may be accomplished via several modalities, including an anti-rotation flange 608 that may be inserted into ports 607 that are located along both the anterior and posterior aspects of stem 603 (see FIG. 13). Flange 608 may be positioned at various locations proximally from bearing housing member 602, for example, 1.5 cm, 2.5 cm and 3.5 cm.

As seen in FIG. 11, in addition to flange ports 607, a plurality of holes 612 are spaced along the medial/lateral aspect of stem 603. These holes are sized to accommodate various transverse fixation devices 609, including for example, screws and pins, which when inserted provide immediate securement of humeral component 600 to the patient's humerus. Generally, the transverse fixation device will inserted through one side of the bone and pass through the stem 603 exiting into the contralateral side of the same bone to provide immediate stability.

The surface of stem 603 may also been coated or have been treated in some fashion to facilitate bone growth and enhance intramedullary fixation. Several methods of surface coating or treatment may be used including for example, porous coating, bead blasting, generated integral nanosurfaces, HA coatings, TCP coatings, BMP coatings as well as other well know in the art bone growth facilitating agents or substrate coatings.

FIGS. 12 and 13 show soft tissue attachment sites 610 on the lateral aspect of 621 of bearing housing member 602. Attachment sites 621 are shown as a hole sized to accommodate various soft tissue connecting mechanisms, including for example, sutures, anchors, clips, tabs and buttons.

Coupling mechanism 511 for prosthesis 50, operates similar to prosthesis 10 through the use of a uniquely configured keyed opening 606 positioned on the posterior aspect of bearing housing member 602 or approximately 270 degrees counter-clockwise relative to the attachment site of stem 603. More specifically, the mechanism involves aligning at about ninety degrees of hyperextension of the prosthesis 50 mating surface 510 with opening 606 of bearing housing member 602. If exact alignment is not achieved, mating surface 510 cannot slide through opening 606 and into inner cavity 611. Once aligned, centralized bearing body 503 is advanced into inner cavity 704 of bearing member 700 that is positioned inside inner cavity 611, and projections 502 and centralized bearing body 503 are nested within inner cavity 704. Ulnar component 500 is then rotated to full extension, resulting in mating surface 510 no longer being aligned and thereby causing the ulnar and humeral components to be moveably connected to form total elbow prosthesis 50.

Essentially, after insertion, centralized bearing body 503 is encapsulated or captured by inner cavity 704 to facilitate smooth sliding articulation between ulnar component 500 and humeral component 600. Positioning opening 606 in the posterior location results in ulnar component 500 being anatomically constrained post-implantation, from rotating to the location of opening 606 and possibly decoupling from humeral component 600.

Humeral component 600 may be constructed from various biocompatible materials including metals (e.g., titanium, cobalt chromium), composites (PEEK), polymers (UHM-WPE, Delrin) or elastomers, as well as combinations of these materials.

FIG. 10 a posterior view of two embodiments of the total elbow prosthesis showing extended medial and lateral aspects of holder end 201, 601 of the humeral component. Positioned on the extended medial and lateral aspects 221, 621 of holder end 201, 601 are means for attachment of soft tissue 210, 610, including ligaments, tendons and other stabilizing structures. As shown in FIG. 10, the means for attachment are through holes 210, 610 that allows the surgeon to pass through wires or sutures to connect the anatomic structures directly to humeral component 200, 600. Additional means of attachment may be positioned along the extended medial and lateral aspects, including, but not limited to tabs, hooks and slots.

Figure 15:
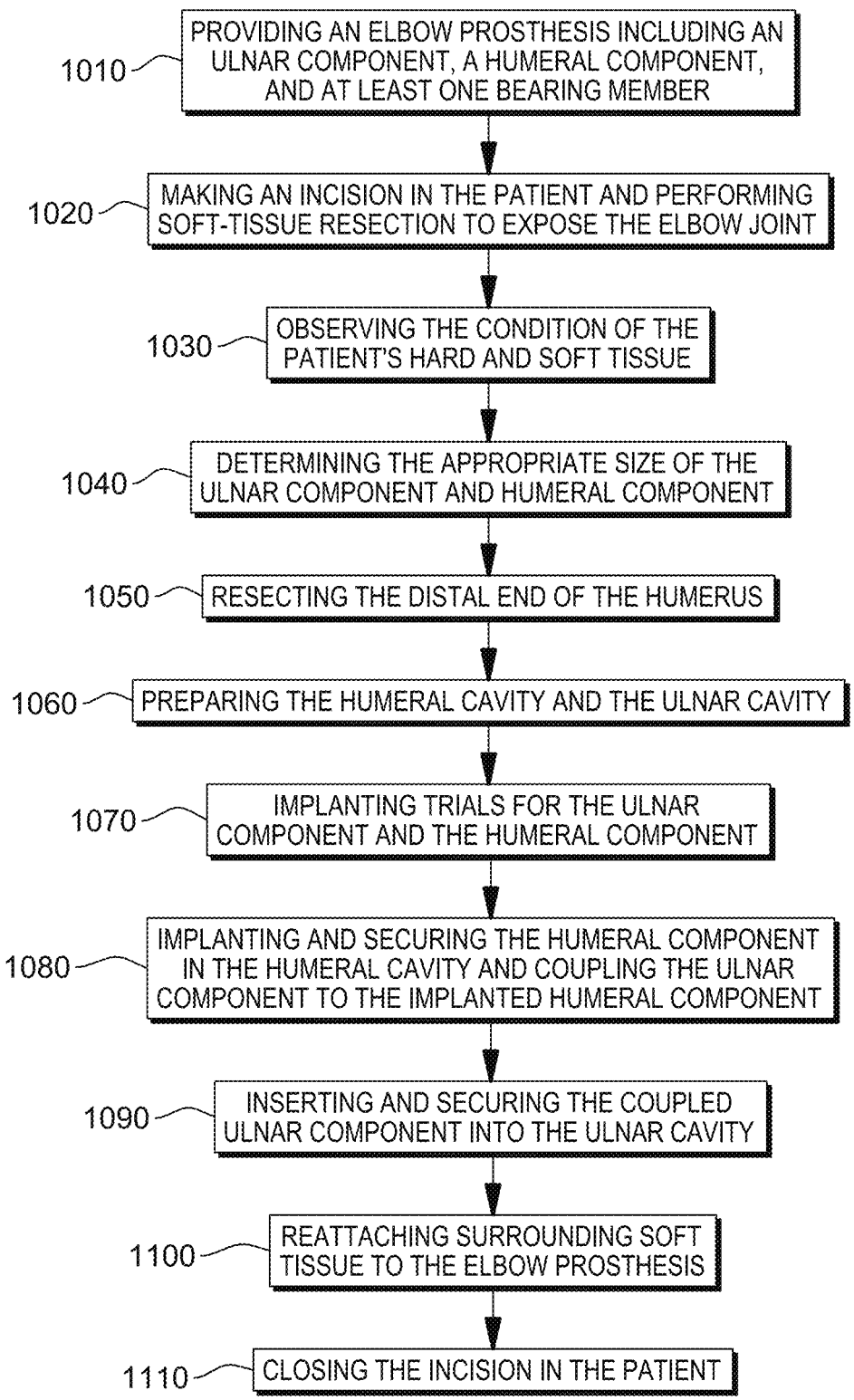
FIG. 15 is a flow chart of a method for performing an elbow arthroplasty, in accordance with an aspect of the present invention.

The example surgical method for using elbow prosthesis 10, 50 is well known in the art, including the appropriate surgical exposure and dissection techniques. As described in FIG. 15, the method 1000 includes, obtaining an elbow prosthesis 1010 that may include an ulnar component, a humeral component and at least one bearing member. The method 1000 may include the step of making an incision in the patient at the elbow 1020 and using for example, a triceps sparing approach or the triceps off technique.

Upon exposing the elbow, the surgeon will look and assess the condition of the ulna and humerus to determine the degree of hard and soft tissue resection that may be necessary 1030. The integrity of the surrounding soft tissue is evaluated to determine if further repairs may be necessary, as well making every attempt to preserve the supporting ligamentus structures.

The method 1000 may then include the step of determining the appropriate size of ulnar component and humeral component using diagnostic imaging and sizing trials 1040.

The method 1000 may include the step of resecting the distal end of the humerus or removing fracture fragments to expose the distal end 1050.

A further step of the method 1000 may include preparing the humeral cavity and the ulnar cavity to allow for implantation of the two components 1060. Various sizes of rasps and/or broaches with self-centering reamers or other canal cutting devices may be used as well as a guiding/drilling device may be utilized to ensure proper placement and alignment of the humeral component and if necessary, distal/proximal fixation devices that may be inserted transverse to the stems of the humeral and ulnar components.

Following cavity preparation, the method 1000 may include the step of implanting the trials for the humeral component and the ulnar component to assess soft tissue balance, range of motion, joint spacing and stability 1070.

The method 1000 may further include the step of implanting the humeral component and securing the component within the intramedullary canal as well as coupling the ulnar component to the implanted humeral component 1080. Depending on the state and integrity of the surrounding soft-tissue, the step may also include attaching or coupling the non-implanted ulnar component to the implanted humeral component. The coupling process would be accomplished by aligning the coupling mechanism 111 which includes the centralized bearing body with the holder end, but more specifically for prosthesis 10 this involves aligning mating surface 110 of bearing body 103 with slot 302 and top surface of slot 303 of bearing member 300 which is positioned at about ninety degrees of hyperextension of the implant. Once aligned, bearing body 103 is inserted between arms 215 and is positioned adjacent to bearing members 300. For prosthesis 50, this involves aligning at about ninety degrees of hyperextension of the implant, bearing body 503 with opening 606. Once aligned, bearing body 503 is inserted into inner cavity 611 and ulnar component 500 is rotated to full extension, resulting in the two components being moveably connected.

Following the implantation of the humeral component and the coupling of the ulnar component to the humeral component, the next step may be to insert and secure in the prepared intramedullary canal of the ulna the ulnar component 1090. A guiding/targeting system may be used for insertion of any proximal/distal fixation devices through the ulnar stem.

The sequence of implanting the ulnar and humeral components may vary depending on surgeon preference and the clinical presentation of the anatomy. Further, the surgeon may also decide to delay the component coupling step until both components are implanted within the ulna and humerus and then hyper-extend the ulna to a point approaching ninety degrees past full extension at which time the coupling mechanism can be actuated, thereby securing the two components together and reestablishing connectivity of the joint. This alternative coupling procedure is dependent upon the clinical condition of the presented elbow joint.

The method 1000 may also include the step of attaching the surrounding soft tissue to the elbow prosthesis and balancing the soft tissue structures to reestablish the joint range of motion and stability 1100.

Upon completion of the joint assessment and observation of the functionality of the implant, including fixation of the components within the ulna and humerus, the step of closing the incision is typically taken 1110.

It would be understood to those skilled in the art that a surgical kit that includes a plurality of various sizes of ulnar and humeral components including modular stems, antirotation flanges and fixation devices may be obtained by the surgeon instead of a single elbow prosthesis to allow for additional flexibility during the operative procedure. Corresponding component trials, broaches, canal centralizing style reamers, soft tissue anchoring devices, including sutures and other devices, and a guiding system for fixation device targeting and implantation may also be part of such a kit.

In accordance with another aspect of the present invention, a total elbow prosthesis kit is described herein. The kit may include a plurality of humeral components, each having a different sized and configured proximal stems. The proximal stems may be either integrally fixed to the holder end, or alternatively, the proximal stems may be modular and configured to be detachably coupled to the holder end. As described above, the modular proximal stem embodiments may have various lengths, diameters, cross-sectional geometries, coatings, fixation locations and linearity over the length of the stem. The kit may also include for the modular humeral design, various sizes and configurations of the holder end, including width, thickness and outside configuration.

The kit may also include, a plurality of ulnar components, each having a different sized and configured distal stem. Distal stems may be integrally fixed to bearing body, or alternatively, distal stems may be modular and configured to be detachably coupled to the bearing body. Distal stems may have various lengths, diameters, cross-sectional geometries, coatings, fixation locations and linearity over the length of the stem. Also, the distal stems may be configured with threads or other fixation mechanisms, like circumferential flanges, fins, ribs, etc. to gain immediate fixation within the intramedullary canal of the ulna. When the distal stem is configured as a screw like member, the stem will include a head that will lock within the stem connector member. The kit may also include a plurality of threaded distal stems that have varying thread patterns, pitches and thread types and depths. (i.e., cancellous threads and cortical threads).

The kit may further include a plurality of detachably coupled anti-rotation flanges that may be fixed to either the humeral proximal stem and/or the ulnar distal stem. Additionally, the kit may also include various sized transverse fixation devices that may be configured, for example, as screws, pins and posts.

The kit may include a corresponding trial system for the ulnar and humeral components, with the trials matching the implants to allow the operating surgeon the ability to use the trials to ensure proper sizing, range of motion and soft-tissue balancing. Other associated instrumentation would be included in the kit, including, for example, a guiding/targeting/drilling instrument for use to ensure proper placement of any fixation devices through the stems of the components. Rasps, broaches, self-centering canal reamers and cutting jigs for bone resection and preparation of the humeral and ulnar intramedullary canals will also be included in the kit. Additionally, tissue attachment mechanisms and devices may also be included in the kit. Examples of these devices include sutures, buttons, tacks, anchors. These devices would facilitate attachment of the surrounding soft-tissue to the implanted elbow prosthesis.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A method for using an elbow prosthesis in a patient, the method comprising:
    obtaining the elbow prosthesis comprising:
        an ulnar component having a bearing end and a stem, wherein the stem is coupled to the bearing end and extends away from the bearing end;
        a humeral component having a holder end and a stem, wherein the stem extends away from the holder end; and
        at least one bearing member coupled to the holder end;
        wherein the bearing end is configured to be coupled within the holder end to articulate against the at least one bearing member;
    making an incision in the patient;
    determining the proper size for the ulnar component and the humeral component;
    preparing an ulna and a humerus of the patient;
    securing the humeral component into the humerus of the patient;
    attaching the ulnar component to the humeral component comprises:
        rotatably coupling the ulnar component to the humeral component; and
        securing the at least one bearing member to an inner surface of the holder end;
    rotating the ulnar component from ninety degrees of hyper-extension with respect to the humeral component into extension;
    rotating the ulnar component from extension into flexion to couple the ulnar component to the humeral component;
    securing the ulnar component into the ulna of the patient; and
    closing the incision in the patient.

2. The method of claim 1, further comprising:
    assessing the condition of the ulna and the humerus to determine the degree of hard and soft tissue resection.

3. The method of claim 1, wherein determining the proper size for the ulnar component and the humeral component comprises using at least one of diagnostic imaging and sizing trials.

4. The method of claim 1, wherein preparing the humerus of the patient comprises resecting a distal end of the humerus and removing fracture fragments to expose the distal end of the humerus.

5. The method of claim 1, further comprising:
    implanting trials for the humeral component and the ulnar component; and
    assessing at least one of soft tissue balance, range of motion, joint spacing, and stability.

6. A method for using an elbow prosthesis in a patient, the method comprising:
    obtaining the elbow prosthesis comprising:
        an ulnar component having a bearing end and a stem, wherein the stem is coupled to the bearing end and extends away from the bearing end;
        a humeral component having a holder end and a stem, wherein the stem extends away from the holder end; and
        at least one bearing member coupled to the holder end;
        wherein the bearing end is configured to be coupled within the holder end to articulate against the at least one bearing member;
    making an incision in the patient;
    determining the proper size for the ulnar component and the humeral component;
    preparing an ulna and a humerus of the patient;
    securing the humeral component into the humerus of the patient;
    attaching the ulnar component to the humeral component;
    securing the ulnar component into the ulna of the patient prior to attaching the ulnar component to the humeral component, wherein the ulna with the secured ulnar component is hyper-extended to enable actuation of the bearing end relative to the holder end to couple the ulnar component to the humeral component; and
    closing the incision in the patient.

7. The method of claim 1, further comprising:
    using a guiding system for inserting at least one fixation device into the stem of the ulnar component.

8. The method of claim 1, further comprising:
    attaching surrounding soft tissue structures to the elbow prosthesis.

9. The method of claim 8, further comprising:
    balancing the soft tissue structures of the elbow of the patient.

10. The method of claim 9, further comprising:
    assessing the joint and functionality of the implanted elbow prosthesis.

11. A method for implanting an elbow prosthesis in a patient, the method comprising:
    obtaining an elbow prosthesis comprising:
        an ulnar component having a bearing end and a stem, wherein the stem is coupled to the bearing end and extends in a distal direction from the bearing end;
        a humeral component having a holder end and a stem, wherein the stem extends in a proximal direction from the holder end; and
        a coupling mechanism, the coupling mechanism comprises at least one bearing member, the bearing end, and the holder end;

wherein the at least one bearing member is positioned within the holder end and the bearing end is configured to be rotatably coupled within the holder end and articulate against the at least one bearing member;
making an incision in the patient;
determining the proper size for the ulnar component and the humeral component;
preparing an ulna and a humerus of the patient;
securing the humeral component into the humerus of the patient and rotatably coupling the ulnar component to the humeral component;
securing the at least one bearing member to an inner surface of the holder end by positioning the at least one bearing member at approximately ninety degrees of hyperextension from the humeral component;
inserting the bearing end of the ulnar component into the holder end of the humeral component adjacent to the at least one bearing member;
rotating the ulnar component relative to the humeral component to lock the ulnar component to the humeral component;
securing the ulnar component in the ulna of the patient; and
closing the incision in the patient.

12. A method for inserting an elbow prosthesis in a patient, the method comprising:
obtaining the elbow prosthesis, the prosthesis comprising:
an ulnar component having a bearing end and a stem, wherein the stem is coupled to the bearing end and extends in a direction opposite the bearing end, and wherein the bearing end comprises a bearing body, the bearing body having a bearing surface and a mating surface, the bearing surface is convex and configured as one of a spherical shape, an oval shape or an elliptical shape, and the mating surface is substantially planar;
a humeral component having a holder end with at least one bearing member coupled to the holder end, a stem, and at least one arm connecting the at least one bearing member to the stem, wherein the stem extends in a direction opposite the holder end; and
a coupling mechanism, the coupling mechanism comprises the at least one bearing member, the bearing body, and the holder end, wherein the at least one bearing member is positioned within an opening disposed on a posterior aspect of the humeral component and the corresponding mating surface disposed on the bearing body;
the bearing end is configured to be coupled within the holder end and slide against the at least one bearing member;
the bearing body further comprising a means for alignment with the at least one bearing member; and
the means for alignment comprising at least one projection extending away from the bearing surface in at least one of a lateral or medial direction;
making an incision in the patient;
determining the proper size for the ulnar component and the humeral component;
preparing the ulna and the humerus of the patient;
securing the humeral component into the humerus of the patient and coupling the ulnar component to the humeral component;
securing the ulnar component in the ulna of the patient; and
closing the incision in the patient.

13. The method of claim 12, wherein attaching the ulnar component to the humeral component comprises coupling the ulnar component to the humeral component secured into the humerus of the patient.

14. The method of claim 13, wherein coupling the ulnar component to the humeral component comprises aligning the coupling mechanism.

15. The method of claim 14, wherein aligning the coupling mechanism comprises aligning the mating surface of the bearing body with at least one slot of the at least one bearing member, inserting the bearing body between the at least one arm, and positioning the bearing body adjacent to the bearing members.

16. A method of assembling an elbow prosthesis, the method comprising:
obtaining an ulnar component comprising a bearing end and a stem, wherein the stem is coupled to the bearing end and extends distally from the bearing end and the bearing end comprises at least one projection extending in at least one of a lateral or medial direction from the bearing end;
obtaining a humeral component comprising a holder end and a stem, wherein the stem extends proximally from the holder end and the holder end comprises at least one notch;
obtaining at least one bearing member with an articulating surface and a slot extending from an exterior side of the bearing member into the articulating surface;
inserting the at least one bearing member into the holder end of the humeral component;
positioning the at least one bearing member at approximately ninety degrees of hyperextension relative to the humeral component;
aligning a mating surface of the bearing end with the slot of the at least one bearing member and aligning the at least one projection with the at least one notch;
sliding the at least one projection of the bearing end into the slot of the at least one bearing member and the at least one projection into the at least one notch; and
rotating the ulnar component with respect to the humeral component to secure the ulnar component to the humeral component.

17. The method of claim 6, further comprising:
assessing the condition of the ulna and the humerus to determine the degree of hard and soft tissue resection.

18. The method of claim 6, wherein determining the proper size for the ulnar component and the humeral component comprises using at least one of diagnostic imaging and sizing trials.

19. The method of claim 6, wherein preparing the humerus of the patient comprises resecting a distal end of the humerus and removing fracture fragments to expose the distal end of the humerus.

20. The method of claim 6, further comprising:
implanting trials for the humeral component and the ulnar component; and
assessing at least one of soft tissue balance, range of motion, joint spacing, and stability.

21. The method of claim 6, further comprising:
using a guiding system for inserting at least one fixation device into the stem of the ulnar component.

22. The method of claim 6, further comprising:
attaching surrounding soft tissue structures to the elbow prosthesis.

23. The method of claim 22, further comprising:
balancing the soft tissue structures of the elbow of the patient.

24. The method of claim 23, further comprising:
assessing the joint and functionality of the implanted elbow prosthesis.

\* \* \* \* \*